United States Patent [19]

Salpekar et al.

[11] Patent Number: 4,631,284
[45] Date of Patent: Dec. 23, 1986

[54] ACETAMINOPHEN COMPOSITIONS CONTAINING LOW DOSES OF CHLORPHENIRAMINE MALEATE, METHOD FOR PREPARING SAME AND TABLETS FORMED THEREFROM

[75] Inventors: Anil M. Salpekar, Creve Coeur, Mo.; John Johnson, Collinsville, Ill.

[73] Assignee: Mallinckrodt, Inc., St. Louis, Mo.

[21] Appl. No.: 755,743

[22] Filed: Jul. 16, 1985

Related U.S. Application Data

[63] Continuation of Ser. No. 672,563, Nov. 19, 1984, abandoned.

[51] Int. Cl.⁴ ............... A61K 31/16; A61K 31/435; A61K 31/135
[52] U.S. Cl. .................... 514/277; 514/629; 514/646; 514/849; 424/80
[58] Field of Search ............ 424/80, 256, 320; 514/277, 849, 646, 629

[56] References Cited

U.S. PATENT DOCUMENTS 3,314,852  4/1967  Green et al. ............ 514/258
3,362,880  1/1968  Jeffries .................... 424/19
4,264,573  4/1981  Powell et al. ............ 424/80

FOREIGN PATENT DOCUMENTS

EP40472   11/1981  European Pat. Off. .
EP130683   1/1985  European Pat. Off. .
1140400    1/1969  United Kingdom .
1287431    8/1972  United Kingdom .
1390032    4/1975  United Kingdom .

OTHER PUBLICATIONS

*Handbook of Nonprescription Drugs,* Seventh Edition, 1982 (American Pharmaceutical Association, Washington, D.C.), pp. 160–202.

*Facts and Comparisons,* 1983 (Facts and Comparisons Division, J. B. Lippincott Company, St. Louis, Missouri), pp. 206–214b.

*Primary Examiner*—Ronald W. Griffin
*Attorney, Agent, or Firm*—R. G. Jackson; L. N. Goodwin; R. J. Klostermann

[57] ABSTRACT

Disclosed are an acetaminophen composition containing a minor amount of a pheniramine maleate, a spray-drying method for preparing the composition and orally administerable analgesic antihistaminic tablets formed from the composition.

24 Claims, No Drawings

ACETAMINOPHEN COMPOSITIONS CONTAINING LOW DOSES OF CHLORPHENIRAMINE MALEATE, METHOD FOR PREPARING SAME AND TABLETS FORMED THEREFROM

This is a continuation of application Ser. No. 672,563, filed Nov. 19, 1984, now abandoned.

BACKGROUND OF THE INVENTION

The present invention relates to an acetaminophen composition containing a minor amount of a pheniramine maleate, to a spray-drying method for preparing the composition and to orally administerable analgesic antihistaminic tablets formed from the composition.

Acetaminophen (hereinafter referred to sometimes as N-acetyl-p-aminophenol or simply APAP) is generally non-compressible, especially in forming orally administerable tablets. Pharmaceutical compositions containing high amounts of acetaminophen and low amounts (e.g., 2% or less) of chlorpheniramine maleate (hereinafter sometimes referred to as CPM) are available to the art. A number of such compositions (hereinafter referred to sometimes as high/low APAP/CPM compositions) are commercially available in tablet form. See *Handbook of Nonprescription Drugs*, Seventh Edition, 1982 (American Pharmaceutical Association, Washington, D.C.), pages 160–202, incorporated herein by reference, and *Facts and Comparisons*, 1983 (Facts and Comparisons Division, J. B. Lippincott Company, St. Louis, Mo.), pages 206–214b, also incorporated herein by reference.

However, tabletting of such high/low APAP/CPM compositions is troublesome from a number of standpoints. When such compositions are formed by the relatively inexpensive and simple expedient of dry-blending a large amount of APAP with a low amount of CPM, tablets formed from a given composition exhibit unacceptably high tablet-to-tablet variation in the amount of CPM therein even when the weight of the tablets is carefully controlled to provide minimal tablet-to-tablet weight variation. In attempts to reduce such tablet-to-tablet variation of the amount of CPM, such high/low APAP/CPM compositions have heretofore been prepared using wet granulation processes. However, wet granulation processes are burdensome, expensive, difficult to control and in some instances result in unacceptably high tablet-to-tablet variations in the amount of CPM in the product. Although in cmparison with dry-blending, the wet granulation methods generally result in more uniform distribution of the CPM in the bulk composition and lower tablet-to-tablet variation in the amount of CPM, substantial penalties are incurred in the form of processing which is more expensive, more time consuming and requires additional equipment and steps.

In an effort to overcome the above problems, attempts were made to prepare an acceptable spray-dried high/low APAP/CPM composition on the basis of the teaching of European patent application No. 81301709.2, published Nov. 25, 1981 under publication No. 0 040 472 A2. That application discloses spray-dried compositions comprising agglomerates of N-acetyl-p-aminophenol in a gelatinized starch matrix. As taught therein, the compositions can be prepared by spray-drying a slurry including N-acetyl-p-aminophenol and gelatinized starch and optionally including other active ingredients such as codeine salts.

Thus, an aqueous slurry was prepared containing about 90 parts APAP and about 9.5 parts pregelatinized starch (in accordance with the disclosure in that application) and further including about 0.6 part CPM dissolved therein. Thereafter, the APAP-CPM-starch slurry was spray dried and the resulting particles containing about 0.95–1.1% water were dry blended with 0.25 part stearic acid, 0.2 part sodium lauryl sulfate and 3 parts starch 1500. This procedure was repeated three times, producing three test lots of particulate blends. Tablets were prepared from each of the three blends on a tabletting press. However, tablets from each of these lots were unacceptable for one or more of the following reasons: poor friability, low maximum hardness and high disintegration time. Following these failures to achieve an entirely satisfactory solution to the previously noted problems through application of the teachings of the European patent application, the efforts based thereon were abandoned.

Accordingly, there has remained a substantial need in the art for a direct tabletting high APAP/low CPM composition which can be prepared in a simple, efficient manner and can be directly compressed into tablets having substantial tablet-to-tablet uniformity of the amount of CPM in tablets prepared with an acceptable tolerance on tablet weight, good mold release properties high hardness, low friability and low disintegration time.

It has now been found by practice of the present invention that such direct tabletting high/low APAP/CPM composition can be prepared. The composition of this invention is highly versatile, exhibiting a capability of being readily and effectively dry-blended or otherwise composited with a wide variety of other ingredients, active and inactive, and thereafter formed into tablets having substantial tablet-to-tablet uniformity of the amount of CPM, good mold release properties, and highly suitable values of hardness, disintegration, and friability.

DESCRIPTION OF THE INVENTION

Generally stated, the present invention provides a spray-dried, direct tabletting, free-glowing, particulate pharmaceutical composition having a substantially high amount of acetaminophen and a substantially low amount of a water-soluble pheniramine maleate, and, when prepared in large quantity, being capable of being directly formed into a multiplicity of dosage-form tablets in high-speed tablet-forming operation of pharmaceutical tabletting presses, the pheniramine maleate being present in the composition in such highly uniform distribution throughout that the tablets have such tablet-to-tablet uniformity of the amount of the pheniramine maleate therein that the percent relative standard deviation of said amount is not more than about 3% as determined for a random sample of 10 tablets, the tablets being substantially free of adherence to the press and having high hardness, short disintegration time, and low friability, the composition comprising as components thereof:

(A) acetaminophen in a pharmaceutically effective major amount, (B) a water-soluble pheniramine maleate component in a pharmaceutically effective low amount not exceeding about 5.0% based on the total weight of the acetaminophen, (C) a pharmaceutically acceptable binder-disintegrant agent in an amount effective for imparting said hardness, disintegration time and friability, (D) a pharmaceutically acceptable lubricant in an amount at least sufficient to impart effective mold release properties to said tablets, and (E) water in an amount from about 0.5 to about 1.5% based on the total weight of the composition, the composition being the product of spray drying an aqueous liquid slurry comprising an aqueous liquid medium and said components (A), (B), (C) and (D) dispersed substantially uniformly throughout said medium, the pheniramine maleate being dissolved in said medium.

In another aspect, generally stated, this invention provides a method for preparing a spray-dried, direct tabletting, free-flowing, particulate pharmaceutical composition having a substantially high amount of acetaminophen and a substantially low amount of a water-soluble pheniramine maleate, and, when prepared in large quantity, being capable of being directly formed into a multiplicity of dosage-form tablets in high-speed tablet-forming operation of pharmaceutical tabletting presses, the pheniramine maleate being present in the composition in such highly uniform distribution throughout that the tablets have such tablet-to-tablet uniformity of the amount of the pheniramine maleate therein that the percent relative standard deviation of said amount is not more than about 3% as determined for a random sample of 10 tablets, the tablets being substantially free of adherence to the press and having high hardness, short disintegration time, and low friability. The method comprises:

(1) preparing an aqueous liquid slurry comprising an aqueous liquid medium and components dispersed substantially uniformly throughout said medium, said components comprising:

(A) finely divided acetaminophen in a pharmaceutically effective major amount, (B) a water-soluble pheniramine maleate component in a pharmaceutically effective low amount not exceeding about 5 parts per 100 parts of the acetaminophen, (C) a pharmaceutically acceptable binder-disintegrant agent in an amount effective for imparting said hardness, disintegration time and friability, and (D) a pharmaceutically acceptable lubricant in an amount at least sufficient to impart effective mold release properties to said tablets, such properties including the tablets being substantially free of adherence to the press, said medium being a solvent for said pheniramine maleate component and said last-mentioned component being dissolved in said medium, the total amount of the dispersed components being such that the slurry is spray-dryable; and (2) while maintaining said components in substantially uniform dispersion spray drying said slurry under spray drying conditions such that the resulting spray dried particulate composition includes water in an amount from about 0.5 to about 1.5% based on the total weight of the composition, said components being distributed throughout the particles of said composition such that at least a portion of said lubricant is dispersed within said particles and at least a portion of the lubricant is disposed on the outer surface of said particles.

In still another aspect, generally stated, this invention provides tablets formed from the above described composition.

DETAILED DESCRIPTION OF THE INVENTION AND OF THE MANNER AND PROCESS OF MAKING AND USING IT

The N-acetyl-p-aminophenol component of the present invention is preferably provided in finely divided form, i.e., the APAP is preferably of small particle size. For example, it has been found that if more than 50% by weight of the APAP particles are larger than 200 mesh (U.S. standard sieve) then the spherical conformation of the particles of the composition is adversely affected. For use in the present invention, preferably all of the APAP particles will pass through a 200 mesh screen, more preferably 75% will pass through a 325 mesh screen and most preferably all will pass through a 325 mesh screen.

The APAP may be included in any pharmaceutically effective major amount, for example 70% by weight or more based on the total weight of the composition. APAP may be included in an amount from about 70% to about 98% by weight on the same basis, preferably from about 80% to about 95% on the same basis.

The water-soluble pheniramine maleate component may be for example, pheniramine maleate per se, chlorpheniramine maleate, d-brompheniramine maleate or compatiable mixtures thereof. Chlorpheniramine maleate is preferred.

The pheniramine maleate component may be included in any pharmaceutically effective low amount. In general amounts thereof from about 0.2 to about 6 parts are included, per 100 parts of the APAP. The component is preferably present in an amount from about 0.3 to about 3 parts, more preferably from about 0.5 to about 2 parts, per 100 parts of the APAP in the spray dried composition.

The binder-disintegrant system may be any pharmaceutically acceptable binder-disintegrant system effective for imparting suitable binding and disintegrant properties to the composition. A suitable binder-disintegranting system is partially gelatinized starch (hereinafter sometimes referred to as PGS). Where PGS is employed as the binder-disintegrant, an auxillary binder may be included. Suitable auxiliary binders are, for example, polyvinylpyrrolidone (hereinafer referred to as PVP) and starch which is substantially fully gelatinized. PGS is preferred as the binder-disintegrant system. In general, PVP is prefered as the auxiliary binder.

The partially gelatinized starch component of the direct tabletting composition preferably has a Percent Gelatinization of from about 50 to about 75%. As used herein, the term "Percent Gelatinization" is a measure of the extent of gelatinization of the partially gelatinized starch relative to fully gelatinized starch and means the percent of Starch 1551 by National Starch Company (a full gelatinized starch) required in a two-component mixture thereof with fully non-gelatinized corn starch such that the value of spectrophotometric absorbance for the mixture at a wavelength of 340 nanometers is the same as the spectrophotometric absorbance value exhibited at such wavelength for the partially gelatinized starch being characterized as having a given value (%) of Percent Gelatinization, subject to the provisons (1) that the absorbance values for both such mixture and such partially gelatinized starch (PGS) are measured on samples prepared therefrom by the modified-Shetty procedure described hereinbelow and (2) that the percentage amount of moisture in the sample prepared from such PGS is at least substantially the same as that in the sample prepared from such mixture.

The modified-Shetty procedure referenced above is a modification of the procedure for determining the degree of starch gelatinization set forth in Shetty et al., "Determining the Degree of Starch Gelatinization," *Cereal Chemistry*, Vol. 51, No. 3, pp. 364–375 (1974), incorporated herein by reference. Briefly stated, the procedure set forth in the above-cited shetty et al. article includes selective digestion of the starch with DIAZYME® glucoamylase (Miles Laboratories) to release D-glucose, working-up the digested starch, treating the digested and worked-up starch with Worthington Reagent to impart spectrophotometric absorbancy to the treated starch and subjecting the resulting sample to spectrophotometry. In the modified-Shetty procedure the following modifications are employed:

(1) Initially, three portions of the starch are washed with 100 ml methanol and passed through a 5-micron Millipore filter. The washed starch portions are dried for about 16 hours at 50° C. prior to weighing and assaying.

(2) The glucoamylase starch digestion is incubated at 50° C. for 30 minutes.

(3) The spectrophotometric absorbancy is measured at a wavelength of 340 nanometers for each of the three treated portions of the starch and the arithmetic mean of the three absorbance measurements is taken as the "absorbance value" recited above.

Approximate Percent Gelatinization values can be conveniently determined using a correlation graph generated for the following starch standards: fully non-gelatinized corn starch (containing zero % gelatinized starch), fully gelatinized starch (Starch 1551-National), and a set of binary mixtures thereof containing different known amounts of the fully gelatinized starch. For example, absorbance was determined by the modified-Shetty method for a set of standards including such starches individually and binary mixtures thereof containing 20%, 40%, 60% and 80% of Starch 1551. The results were plotted on Cartesian coordinates and showed a substantially linear relationship between the amount, in percent, of fully gelatinized starch and the corresponding absorbancy. Three data-generation runs were made, with correlation factors found for the three runs of 0.9926, 0.9974 and 0.9952. The final correlation graph was a plot of the three-run average absorbances found for each of the six gelatinized starch amounts (0, 20, 40, 60, 80 and 100%) versus such amounts. The spectrophotometric samples prepared from each such standard had moisture contents in the range from about 3 to about 5%. Tests on spectrophotometric samples prepared from Starch 1500 (Colorcon, Inc.) had moisture contents in the 3 to 5% range and the Percent Gelatinization of that herein preferred partially gelatinized starch was approximated as 57.7%, the value of % fully gelatinized starch on the final correlation graph for the average absorbance found for the samples prepared from Starch 1500.

The partially gelatinized starch (hereinafter referred to as PGS) serves to impart good binder and disintegrant properties as well as a good balance thereof to the composition, which can be directly tabletted to form tablets having high hardness, short disintegration time and low friability.

The term "direct tabletting" and terms of like import, as used herein, mean that the composition can be formed into a tablet using well known tabletting apparatus and processes without need for addition of any adjuvant material to the composition. Inclusion of PGS having a Percent Gelatinization of less than about 50% (e.g., 45% or less) usually results in unacceptably lower compressibility (as evidenced e.g., by unacceptably lower tablet hardness). Inclusion of PGS having a Percent Gelatinization of more than about 75% (e.g., 80% or more) usually results in unacceptably longer tablet disintegration time. The lower hardness and longer disintegration time are relative to the corresponding tablet hardness and disintegration time obtained under identical tabletting conditions for otherwise identical compositions except that the Percent Gelatinization of the PGS component is within the above range.

The PGS is preferably included in an amount effective for imparting to the composition the capability of being formed into tablets having high hardness (e.g., about 8 kp or more), short disintegration time (e.g., about 10 minutes or less) and low friability (e.g., about 1% or less).

As used herein, the term "kp" means kiloponds, a well known unit of force for expressing hardness or crushing strength of pharmaceutical tablets when such hardness is determined on a Schleuniger Tablet Hardness Tester.

In general, such effective amount of PGS is from about 5 or less to about 20 or more parts per 100 parts of the APAP component.

Partially gelatinized starch suitable for use in the composition can be prepared using any suitable starch-gelatinization method and stopping the gelatinization when the desired Percent Gelatinization has been obtained. A suitable PGS is also commercially available from Colorcon, Inc., West Point, Pa. as Starch 1500 (preferred).

The lubricant component may be any pharmaceutically acceptable lubricant, which may be, e.g. hydrophilic or hydrophobic. This component is present in a lubricating amount at least sufficient to impart mold release properties to tablets formed of the compositions and preferably insufficient to increase disintegration time and dissolution time of such tablets, and preferably insufficient to decrease the hardness obtainable for tablets formed from compositions of this invention containing lower lubricating amounts of the same lubricant.

Suitable lubricants for use as the lubricant component include, for example, stearic acid; metallic stearate (such as sodium, calcium, magnesium and zinc stearate, etc.); sodium lauryl sulfate, polyethyleneglycol; hydrogenated vegetable oils; talc; and compatible mixtures of two or more such materials. Stearic acid is preferred.

In general, the stearic acid or other lubricant component may be present in an amount from about 0.10 to about 2 parts, preferably from about 0.1 to about 1 part, per 100 parts of APAP.

The composition also includes water in an amount effective for aid in direct tabletting. Such effective amount is, in general, found to be from about 0.5 to about 1.5% based on the total weight of the composition, preferably about 1.0% on the same basis.

Optionally, the composition may further include a pharmaceutically acceptable compressibility-promoting binder as an additional binding agent in an amount effective for increasing the obtainable hardness of tablets formed from the composition.

Materials suitable for use as the optionally included, but preferably included additional binder agent include, for example, substantially (fully gelatinized starches) (e.g. starches which are at least 98% and preferably at least 99% gelatinized) such as substantially fully gelatinized starch paste and substantially fully gelatinized pregelatinized starch; polyvinylpyrrolidone; hydroxypropylmethylcellulose; hydroxypropylcellulose; gelatin; natural gums (e.g., gum acacia, gum tragacanth, etc.); sucrose; mannitol; ethylcellulose; synthetic polymer binders commonly used in the industry; and compatible mixtures of two or more such materials. Polyvinylpyrrolidone (PVP) is most preferred (preferably PLASDONE ® PVP K29-32 by GAF Corp.). Another preferred auxiliary binder is pregelatinized starch which is at least substantially fully gelatinized and preferably 100% gelatinized.

In general, such effective amount of optional binder is from about 0.5 or less to about 5 or more parts, preferably from about 0.5 to about 4 parts, per 100 parts of the APAP component.

Optional or auxiliary binders preferably are not included in an amount in excess of 25 parts per 100 parts of the PGS component, especially where fully gelatinized starch (pregelatinized or otherwise) is employed as the optional binder.

As a further option, the composition may further include a pharmaceutically acceptable disintegration-promoting material as an additional disintegration agent in an amount effective for decreasing the obtainable disintegration time of tablets formed from the composition.

Materials suitable for use as the optionally included, but preferably included, additional disintegration agent include, for example, starch (e.g., corn starch and other non-gelatinized starches), sodium carboxymethyl starch (sodium starch glycolate); microcrystalline cellulose; cross-linked cellulose; cross-linked polyvinylpyrrolidone; soy protein; alginic acid and compatible mixtures of two or more of such materials. Cross-linked polyvinylpyrrolidone (hereinafter referred to as XL-PVP), sometimes referred to in the art as cross-linked povidone, is preferred (preferably POLYPLASDONE XL TM cross-linked N-vinyl-2-pyrrolidone from GAF Corporation).

In general, such effective amount of the optional or auxiliary disintegration agent is from about 1 or less to about 5 or more parts, preferably about 2.2 parts, per 100 parts of the APAP.

In a preferred embodiment, the composition includes the following components in the amounts indicated (together with water in an amount from about 0.5 to about 1.5% based on the total weight of the composition):

| COMPONENTS | APPROXIMATE AMOUNTS | |
|---|---|---|
| | (a) | (b) |
| APAP (acetaminophen) | 100 | 325 |
| Chlorpheniramine maleate | 0.2-6 | 0.6-20 |
| Partially gelatinized starch | 5.2-20 | 17-65 |
| Stearic Acid | 0.1-1.5 | 0.3-4.9 |
| Polyvinylpyrrolidone | 0.5-4 | 1.6-13 |

The amounts shown are in parts per (a) 100 parts of APAP and per (b) 325 parts of APAP, respectively.

The best embodiment composition of this invention contemplated at the time of executing this patent application is as follows, wherein the amounts given are in parts per (a) 100 parts (dry basis) of the composition, per (b) 100 parts of APAP, and (c) per 325 parts of APAP, respectively:

| COMPONENTS | APPROXIMATE AMOUNTS | | |
|---|---|---|---|
| | (a) | (b) | (c) |
| APAP (acetaminophen) | 90 | 100 | 325 |
| Chlorpheniramine maleate | 0.56 | 0.62 | 2 |
| Partially gelatinized starch | 8.24 | 9.2 | 29.8 |
| Stearic Acid | 0.2 | 0.22 | 0.7 |
| Polyvinylpyrrolidone | 1.0 | 1.1 | 3.6 |

The last-given embodiment includes water in an amount desirably from about 0.5 to about 1.5%, preferably about 1% based on the total weight (dry basis) of the composition. Such composition of the last-given embodiment can be repeatedly, in general, formed into tablets having hardness of 12 kp or more (often 14 kp or more) and having disintegration time of 10 minutes or less (often 6 minutes or less) at 12 kp hardness.

In use, the compositions of this invention advantageously may be composited with other active or inactive ingredients, either prior to compositing the components to form the composition or after the composition is formed (e.g., by dry blending the composition with such ingredients) and thereafter directly compressed into tablets having eminently suitable values of hardness and disintegration time for a variety of end-use applications.

The composition of this invention may further include, for example, compatible sympathomimetic agents (e.g., phenylpropanolamine hydrochloride, phenylephrine hydrochloride, pseudoephedrine hydrochloride and the corresponding sulfates); antitussive agents (e.g. dextromethorphan hydrobromide and the like); and compatible mixtures of two or more of these materials. Such agents may be included in any suitable pharmaceutically acceptable amount for example, from about 1 to about 30 parts or more per 100 parts APAP.

The compositions of this invention are preferably made by the method set forth in the above section entitled "Description of the Invention", i.e., including a spray drying step.

Where a partially gelatinized starch is included, the slurry preparation step is preferably carried out in a manner to achieve substantially complete hydration of the partially gelatinized starch component, preferably using a low shear mixing action so as not to increase the Percent Gelatinization of the PGS, at least not to increase it above the maximum desired percent gelatinization of about 75%. Preferably, the stearic acid is thoroughly mixed in the slurry, i.e., substantially uniformily dispersed throughout the aqueous medium (e.g., water) employed.

In the preferred embodiment of the method of this invention, the following procedure is followed.

Slurry Makeup (A) To a suitable blender add the binder-disintegrant system (e.g., partially gelatinized starch) and an equal amount of acetaminophen. Thereafter, add the lubricant (e.g., stearic acid) with stirring until a uniform blend is obtained.

(B) Dissolve the water-soluble components (including the pheniramine maleate component and any optionally included water-soluble components, e.g., polyvinylpyrrolidone) in water, and, thereafter, add the resulting solution to the blend from step A with agitation or mixing.

(C) To the mixture resulting from step B add the balance of the acetaminophen while mixing is continued.

(D) Preferably, the agitation is continued until the resulting slurry is smooth.

Spray drying conditions will be dependent on various factors, such as feed slurry concentration, method of atomization, type of spray dryer, desired rate of drying, relative humidity, and other factors which will be readily apparent to those skilled in the art.

Preferred spray drying conditions are set forth in the table below, along with an effective range of conditions for each condition or parameter indicated, by way of example for a counter-current spray dryer operated at a slurry feed rate of about 10 kilograms per hour:

| Spray Drying Conditions | Preferred | Range |
|---|---|---|
| Feed slurry concentration | 52% | 35–60% |
| Inlet air temperature | 430° F. | 375° F.–600° F. |
| Outlet air temperature | 200° F. | 150° F.–250° F. |
| Atomization pressure | 28 psi | 20–35 psi |
| Feed Pressure | 52 psi | 40–60 psi |
| Feed Slurry temperature | 82° F. | 60° F.–100° F. |
| Feed Slurry viscosity | 2100 cp | 1500–3000 cp |

Practice of the present invention is illustrated by the following specific, but non-limiting examples. All amounts (including parts, %, etc.) given in the examples and throughout this disclosure, including the claims which follow, are by weight unless indicated otherwise.

Unless indicated otherwise, the compositions in each of the following Examples were prepared using the above described preferred method. This includes the steps of forming each slurry and spray drying the resulting slurry employing the preferred conditions. Also, in each example unless indicated otherwise, spray drying was effected using counter current spray drying in a counter-current spray dryer fitted with a two-fluid mozzle for slurry atomization, manufactured by Niro Atomizer Company (Model No. 6903), in accordance with the manufacturer's instructions for use.

The PGS employed was Starch 1500 (Colorcon, Inc.) having an approximate Percent Gelatinization of 52–75%.

All tablets were formed on a Manesty B3B 16-station rotary tablet press (commercially available from Thomas Engineering Company) in accordance with the manufacturer's instructions for use. The press was fitted with a tablet tooling designed to make cylindrical tablets, each tablet having opposite bevel-edge flat faces and overall diameter of 13/32 inch. The press was operated to form tablets having a nominal weight of about 360 mg unless otherwise indicated.

As used herein, the following terms have the meanings indicated:

(A) "disintegration time" means the time measured using the distintegration-time test method set forth in U.S. Pharmacoepia (hereinafter "USP") XX for uncoated tablets except that the disks are not employed;

(B) "hardness" means the hardness measured on a Schleuniger hardness tester;

(C) "maximum hardness" means the maximum hardness at which the tablets are substantially free of lamination;

(D) "friability" means the friability measured on a Roche Friabulator for 20 tablets and 100 revolutions.

In the Examples, unless otherwise indicated all tablet hardness values are averages for 10 tablets and tablet disintegration times were measured for tablets having about 8 kp to 12 kp hardness.

EXAMPLE 1

Compositions of this invention were prepared following the example preparation method referenced above. Shown in table below are the components employed in the indicated amounts, together with measured tabletting results.

| Component | APPROXIMATE AMOUNTS (per 100 parts APAP) |
|---|---|
| APAP | 100 |
| CPM | 0.62 |
| PGS | 9.2 |
| (Percent Gelatinization) | (52–75) |
| Stearic Acid | 0.22 |
| Water | 0.53[a] |
| PVP (Aux. Binder) | 1.1 |
| Tablet Results | |
| Hardness (kp), average | 8.6 |
| Disintegration Time (Minutes:Seconds) | 3:20 |
| Friability (%) | 0.10 |

[a] percent, based on the total weight of the composition

EXAMPLE 2

Additional tablets were formed from the composition of Example 1 employing increased tabletting compression force. The maximum hardness thus determined was 13.2 kp, with a corresponding disintegration time of 7 minutes, 15 seconds.

EXAMPLE 3

A portion of the composition prepared in Example 1 was exposed to moist air. The resulting composition was substantially identical to that of Example 1 except that the amount of water was 0.74%, based on the total weight of the composition.

Results for tablets prepared from this composition were 8.6 kp average hardness, 0% friability, and 3 minutes, 45 seconds disintegration time. The maximum hardness (determined as in Example 2) for tablets prepared from this composition was 17.2 kp.

The compositions of Examples 1 and 3 were observed to be substantially free of adherence to the tabletting press during tabletting.

In another embodiment, the compositions of this invention can be prepared by co-current spray drying of slurries prepared as set forth above.

Preferred co-current spray drying conditions are set forth in the table below for a slurry feed rate of about 400 kilograms per hour, along with an effective range of conditions for each condition or parameter indicated:

| | Approximate Conditions | |
|---|---|---|
| | Preferred | Range |
| Feed slurry concentration | 53% | 35–60% |

| | Approximate Conditions | |
|---|---|---|
| | Preferred | Range |
| Inlet air temperature | 520° F. | 300° F.–600° F. |
| Outlet air temperature | 200° F. | 150° F.–250° F. |
| Atomization pressure | 2100–2600 psi | 1000–4000 psi |

EXAMPLE 4

In this example, the following particulate composition of this invention was prepared using substantially the same method employed in Example 1 except co-current spray drying was employed at a slurry feed rate of approximately 400 kg/hr.

The composition is set forth below:

| Component | APPROXIMATE AMOUNTS (per 100 parts APAP) |
|---|---|
| APAP | 100 |
| CPM | 0.6 |
| PGS (Starch 1500 - Colorcon, Inc.) | 9.1 |
| Stearic Acid | 0.2 |
| Water (% d.b. of dried composition) | 1.1 |
| PVP (Aux. Binder) | 1.1 |

The co-current spray dryer employed was an 8-foot Procter & Schwartz tower dryer equipped with an SF90 spray nozzle. The concentratin of the feed slurry, which was continuously agitated and at a temperature of about 70°–85° F. throughout the spray drying process, was about 52.2% solids. The slurry viscosity was about 2100 centipoises at 82° F. The dryer was operated at the following approximate conditions: inlet air temperature (497° F.), outlet air temperature (192° F.) and feed pressure or atomization pressure (2300 psig).

A large quantity (about 800 kg) of the composition was prepared and continuously collected in drums fitted with plastic liners, each drum containing about 50 kilograms of the composition.

Samples of the composition, each weighing generally about 50–75 grams, were taken from fourteen consecutively filled drums (one sample per drum) beginning with the second drum. These samples were asseyed for amounts and uniformity of selected components with the following averaged results wherein the percentage amounts for the indicated component are based on the total weight of each composition sample: water (1.10%), APAP (90.86%) and CPM (0.542%). The calculated percent relative standard deviations (% RSD) for these components were as follows: water (14.2% RSD), APAP (1.06% RSD) and CPM (0.58% RSD).

Average cumulative particle size distribution results obtained were as follows (for the composition):

| +60 mesh | +100 mesh | +200 mesh | +325 mesh |
|---|---|---|---|
| 17.7% (3.4% RSD) | 65.2% (3.5% RSD) | 91.5% (1.9% RSD) | 97.9% (1.1% RSD) |

A multiplicity of tablets of the particulate composition of this example were prepared at high speed. The weight of the tablets was approximately 361 mg. and substantially uniform from tablet-to-tablet. Tablet properties (approximate values) obtained are set forth below for tablets compressed to different extents. Compressive tabletting force was increased sequentially (and tablet thickness decreased suquentially) from Group 1 to Group 4.

| Group | Average Hardness (kp) | Friability (%) | Disintegration Time (Min:Sec.) |
|---|---|---|---|
| 1* | 10.3 | 0.12 | 6:35–8:00 |
| 2 | 11.3 | 0.22 | 5:30–6:35 |
| 3 | 13.7 | 0.07 | 5:20–8:10 |
| 4 | 20** | — | — |

*The material from which tablets were formed in this group had decreased in the amount of water to 1.02% at time of tabletting.
**Maximum hardness greater than 20.

The composition of this example was observed to be substantially free of adherence to the press during tabletting.

A portion of the tablets were collected in capped bottles, each containing approximately 250 tablets. From a randomly selected bottle, 10 tablets were randomly selected as a sample for tests of tablet-to-tablet assay uniformity. Each of these tablets was assayed for its ammount of APAP and CPM as a percent of the total weight of the tablet. An additional 25 tablets were randomly selected from the bottle as a sample for tests of tablet-to-tablet weight uniformity. Each of these tablets was separately weighed. The percent relative standard deviations (%RSD) from the corresponding resulting average values were calculated. The results were as follows:

| | AVERAGE | RANGE | % RSD |
|---|---|---|---|
| Tablet Weight | 361.1 mg | 357.9–363.4 | 0.38 |
| CPM | 0.539% | 0.522–0.555% | 1.85 |
| APAP | 92.8% | 91.2–94.5% | 1.2 |

EXAMPLE 5

In this example, the following particulate composition of this invention was prepared using substantially the same procedure employed in Example 1. Shown in the table below are the components employed in the indicated amounts, together with measured tabletting results for three groups of tablets prepared with the compressive force increasing from Group 1 to Group 3.

| Component | APPROXIMATE AMOUNTS (per 100 parts APAP) | | |
|---|---|---|---|
| APAP | 100 | | |
| CPM | 0.63 | | |
| PGS | 10.6 | | |
| (Percent Gelatinization) | (52–75) | | |
| Stearic Acid | 0.25 | | |
| Water | 1.4(a) | | |
| PVP (Auz. Binder) | 1.5 | | |
| Phenylephrine-HCl | 1.6 | | |
| XL-PVP (Aux. Disintegrant) | 3.0 | | |
| Tablet Results | Group 1 | Group 2 | Group 3 |
| Hardness (kp), average | 10.4 | 13.8 | "20"(b) |
| Disintegration Time (Minutes:Seconds) | 5:45 | 6:30 | — |
| Friability (%) | 0.04 | 0.00 | — |
| Weight (mg), average | 387.3 | 386.4 | — |
| Thickness (in.), | 0.178 | 0.172 | 0.157 |

-continued

| | |
|---|---|
| average | |

(a) percent, based on the total weight of the dried composition
(b) greater than 20 kp The composition of this example was observed to be substantially free of adherence to the press during tabletting.

The concentration of the feed slurry, which was continuously agitated and at a temperature of about 70°–90° F. throughout the spray drying process, was about 52.3% solids with water employed as the aqueous liquid medium. The slurry viscosity was about 2900 centipoises at 88° F. The dryer was operated at the following approximate conditions: inlet air temperature (435°–446° F.), outlet air temperature (203°–230° F.), slurry feed pressure (26–56 psig), atomizing air pressure (30–46 psig) and rate (1.5–2.0 cfm), and exhaust air rate (116–120 cfm.).

EXAMPLE 6

The following particulate composition of this invention was prepared using substantially the same procedure employed in Example 1, with the slurry and spray-drying conditions approximately as set forth in Example 5. Shown in the table below are the components employed in the indicated amount.

| COMPONENT | APPROXIMATE AMOUNT (per 100 parts APAP) |
|---|---|
| APAP | 100 |
| d-Brompheniramine maleate | 0.60 |
| PGS (52–75 Percent Gelantinization) | 7.2 |
| Stearic Acid | 0.92 |
| Gelatinized starch, substantially fully gelatinized (Aux. binder) | 5.2 |
| Pseudoephedrine sulfate | 12.0 |
| Water | 0.5–1.5(a) |

(a)%, based on the total weight of the dried composition.

It is contemplated that this composition can be formed into tablets with substantially no adherence to the press and with tablet physical properties as follows: 9 minutes or less disintegration time and 1% or lower friability when the tablets are formed by compressing to a hardness of about 10 to about 15 kp, with maximum hardness of about 18 kp or more.

BEST MODE CONTEMPLATED

The best mode contemplated for carrying out this invention has been set forth in the above description, for example, by way of setting forth preferred materials and operating conditions, including but not limited to preferred ranges and values of amounts and other non-obvious variables material to successfully practicing the invention in the best way contemplated at the time of executing this patent application.

It is understood that the foregoing detailed description is given merely by way of illustration and that many modifications may be made therein without departing from the spirit or scope of the present invention.

What is claimed is:

1. A spray-dried, direct tabletting, free-flowing, particulate pharmaceutical composition having a substantially high amount of acetaminophen and a substantially low amount of a water-soluble pheniramine maleate, and, when prepared in large quantity, being capable of being directly formed into a multiplicity of dosage-form tablets in high-speed tablet-forming operation of pharmaceutical tabletting presses, the pheniramine maleate being present in the composition in such highly uniform distribution throughout that the tablets have such tablet-to-tablet uniformity of the amount of the pheniramine maleate therein that the percent relative standard deviation of said amount is not more than about 3% as determined for a random sample of 10 tablets, the tablets being substantially free of adherence to the press and having high hardness, short disintegration time, and low friability, the composition comprising as components thereof:
   (A) acetaminophen in a pharmaceutically effective major amount,
   (B) a water-soluble pheniramine maleate component in a pharmaceutically effective low amount not exceeding about 5.0% based on the total weight of the acetaminophen,
   (C) a pharmaceutically acceptable binder-disintegrant agent in an amount effective for imparting said hardness, disintegration time and friability,
   (D) a pharmaceutically acceptable lubricant in an amount at least sufficient to impart effective mold release properties to said tablets, and
   (E) water in an amount from about 0.5 to about 1.5% based on the total weight of the composition,
the composition being the product of spray drying an aqueous liquid slurry comprising an aqueous liquid medium and said components (A), (B), (C) and (D) dispersed substantially uniformly throughout said medium, the pheniramine maleate being dissolved in said medium.

2. The composition of claim 1 wherein the pheniramine maleate component is selected from pheniramine maleate, chlorpheniramine maleate, d-bromopheniramine maleate and compatible mixtures thereof.

3. The composition of claim 1 wherein the pheniramine maleate component is chlorpheniramine maleate.

4. The composition of claim 1 wherein the binder-disintegrant agent is partially gelatinized starch.

5. The composition of claim 4 wherein the partially gelatinized starch has a Percent Gelatinization of from about 50 to about 75%.

6. The composition of claim 4 further including a pharmaceuticlly acceptable compressibility-promoting binder as an additional binding agent in an amount effective for increasing the obtainable hardness of tablets formed from the composition.

7. The composition of claim 6 wherein the additional binding agent is selected from polyvinylpyrrolidone, gelatinized starch which is substantially fully gelatinized and mixtures thereof.

8. The composition of claim 7 wherein the additional binding agent is pyrrolidone.

9. The composition of claim 7 wherein the additional binding agent is substantially fully gelatinized starch.

10. The composition of claim 1 further including a sympathomimetric agent selected from the group consisting of phenylpropanolamine, phenylephrine, pseudoephredine, pharmaceutically acceptable salts thereof, and compatible mixtures of two or more of these agents.

11. The composition of claim 10 wherein the sympathomimetric agent is selected from phenylpropanolamine hydrochloride, phenylephrine hydrochloride, pseudoephredine hydrochloride and pseudoephredine sulfate.

12. The composition of claim 1 comprising 100 parts of acetaminophen; from about 0.2 to about 6 parts of a pheniramine maleate component selected from the group consisting of pheniramine maleate, chorpheniramine maleate, d-brompheniramine maleate and mixtures thereof; from about 5 to about 13 parts of a binder-disintegrant agent; and from about 0.1 to about 2 parts oof a lubricant.

13. The composition of claim 12 wherein the binder-disintegrant agent is partially gelatinized starch and further including about 0.5 to about 2 parts of an additional binding agent.

14. The composition of claim 13 wherein the additional binding agent is polyvinylpyrrolidone.

15. A method for preparing a direct tabletting, free-flowing, particulate pharmaceutical composition having a substantially high amount of acetaminophen and a substantially low amount of a water-soluble pheniramine maleate, and, when prepared in large quantity, being capable of being directly formed into a multiplicity of dosage-form tablets in high-speed tablet-forming operation of pharmaceutical tabletting presses, the pheniramine maleate being present in the composition in such highly uniform distribution throughout that the tablets have such tablet-to-tablet uniformity of the amount of the pheniramine maleate therein that the percent relative standard deviation of said amount is not more than about 3% as determined for a random sample of 10 tablets, the tablets being substantially free of adherence to the press and hivin high hardness, short disintegration time, and low friability, said method comprises:

(1) preparing an aqueous liquid slurry comprising an aqueous liquid medium and components dispersed substantially uniformly throughout said medium, said components comprising:

(A) finely divided acetaminophen in a pharmaceutically effective major amount, (B) a water-soluble pheniramine maleate component in a pharmaceutically effective low amount not exceeding about 6 parts per 100 parts of the acetaminophen, (C) a pharmaceutically acceptable binder-disintegrant agent in an amount effective for imparting said hardness, disintegration time and friability, . and (D) a pharmaceutically acceptable lubricant in an amount at least sufficient to impart effective mold release properties to said tablets, such properties including the tablets being substantially free of adherence to the press, said medium being a solvent for said pheniramine maleate component and said last-mentioned component being dissolved in said medium, the total amount of the dispersed components being such that the slurry is spray-dryable; and (2) while maintaining said components in substantially uniform dispersion spray drying said slurry under spray drying conditions such that the resulting spray dried particulate composition includes water in an amount from about 0.5 to about 1.5% based on the total weight of the composition, said components being distributed throughout the particles of said composition such that at least a portion of said lubricant is dispersed within said particles and at least a portion of the lubricant is disposed on the outer surfaces of said particles.

16. The method of claim 15 wherein the slurry contains up to about 60% solids.

17. The method of claim 15 wherein 100% of the finely divided acetaminophen particles will pass through a 200 mesh screen.

18. The method of claim 15 wherein the pehniramine maleate component is selected from pheniramine maleate, chloropheniramine maleate, d-bromopheniramine maleate and compatible mixtures thereof.

19. The method of claim 15 wherein the binder-disintegrant agent is partially gelatinized starch.

20. The method of claim 19 wherein the partially gelatinized starch has a Percent Gelatinization of from about 50 to about 75%.

21. The method of claim 15 wherein the slurry is formed and maintained under forming and maintaining conditions including sufficiently low shear to avoid increasing said Percent Gelatinization above about 75%.

22. A tablet formed from the composition of claim 1.

23. A tablet formed from the composition of claim 12.

24. A pharmaceutical product comprising a multiplicity of orally administerable tablets prepared by tabletting descrete portions of a large quantity of the composition of claim 1.

* * * * *